US006338657B1

United States Patent
Harper et al.

(10) Patent No.: US 6,338,657 B1
(45) Date of Patent: Jan. 15, 2002

(54) HAND PIECE CONNECTOR (75) Inventors: Richard M. Harper, Cincinnati; Robert Perrin Gill, Mason; William T. Donofrio, Cincinnati, all of OH (US)

(73) Assignee: Ethicon Endo-Surgery, Cincinnati, OH (US)

( * ) Notice: Subject to any disclaimer, the term of this patent is extended or adjusted under 35 U.S.C. 154(b) by 0 days.

(21) Appl. No.: 09/693,550

(22) Filed: Oct. 20, 2000

(51) Int. Cl.$^7$ ............................................... H01R 13/04
(52) U.S. Cl. ....................... 439/692; 439/651; 439/598; 439/924.1
(58) Field of Search ................................ 439/692, 680, 439/651, 655, 598, 909, 924.1, 188, 489, 281, 588, 589

(56) References Cited

U.S. PATENT DOCUMENTS

| | | | | |
|---|---|---|---|---|
| 3,315,214 A | * | 4/1967 | Davis | 439/598 |
| 6,048,224 A | * | 4/2000 | Kay | 439/651 |
| 6,056,573 A | * | 5/2000 | Nishioka | 439/924.1 |
| 6,056,599 A | * | 5/2000 | Flickinger et al. | 439/598 |
| 6,116,965 A | * | 9/2000 | Arnett et al. | 439/692 |

* cited by examiner

*Primary Examiner*—Tho D. Ta
(74) *Attorney, Agent, or Firm*—Darby & Darby (57) ABSTRACT

The present invention provides a connector assembly including a connector for use in electrically connecting a surgical instrument to a power source, such as a generator. The connector generally includes an outer shell with a plurality of first and second electrical conductors disposed within the outer shell for providing the electrical connection between the surgical instrument and a cable leading to the power source. In one aspect of the present invention, the connector includes an isolation barrier disposed within the outer shell so as to separate each of the first electrical conductors from each of the second electrical conductors. In another aspect, the connector includes a keying feature in which the outer surface of the outer shell is modified so as to ensure that the connector may only be plugged into the generator a single way. This reduces the risk that the electrical conductors may be bent due to improper orientation during the insertion action. In yet another aspect of the present invention, a member disposed at the end of an instrument cable sealingly mates with one end of the connector to protect the electrical connection between the cable and the conductor. The member has a resilient arm which is attached to a soak cap permitting the opposite end of the connector to be sealed in select conditions.

23 Claims, 7 Drawing Sheets

HAND PIECE CONNECTOR

TECHNICAL FIELD

This invention relates to ultrasonic surgical systems and, more particularly, to a customized hand piece connector for providing an electrical connection between a surgical instrument hand piece and a power source, e.g., a generator, for delivering power to the hand piece.

BACKGROUND OF THE INVENTION

It is known that electric scalpels and lasers can be used as a surgical instrument to perform the dual function of simultaneously effecting the incision and hemostatis of soft tissue by cauterizing tissues and blood vessels. However, such instruments employ very high temperatures to achieve coagulation, causing vaporization and fumes as well as splattering, which increases the risk of spreading infectious diseases to operating room personnel. Additionally, the use of such instruments often results in relatively wide zones of thermal tissue damage. Thus, it is preferable to use instruments which do not have these associated disadvantages.

Cutting and cauterizing of tissue by means of surgical blades vibrated at high speeds by ultrasonic drive mechanisms is also well known. One component of this type of system is an ultrasonic generator which produces an electrical signal of a particular voltage, current and frequency. The generator is connected by a cable to a hand piece, which contains piezoceramic elements forming an ultrasonic transducer. In response to a switch on the hand piece or a foot switch connected to the generator by another cable, the generator signal is applied to the transducer, which causes a longitudinal vibration of its elements. A structure connects the transducer to a surgical blade, which is thus vibrated at ultrasonic frequencies when the generator signal is applied to the transducer. The structure is designed to resonate at the selected frequency, thus amplifying the motion initiated by the transducer.

A connector assembly serves to electrically connect the hand piece to the generator for powering the transducer in the hand piece and causing the necessary mechanical vibrations. Typically, the connector which is used is of a general construction and thus a number of hand pieces from a number of manufacturers may be mated with one specific generator of a preferred type. The connector will often include a number of electrical pins which provide an electrical connection between the hand piece and a mating electrical receptacle provided in the generator. The electrical pins are arranged in various patterns depending upon the application and very often the electrical pins have small diameters and thus are relatively fragile in nature. If a user attempts to insert the connector into the mating receptacle of the generator without having the conductive pins and ports of the mating receptacle properly aligned, the electrical pins will be bent and damaged.

Most types of medical connectors and the respective mating receptacle each have two sets of electrical pins which have two different functions. Each includes a non-isolated set of contacts (pins/contacts) which are referenced to ground and a patient set of contacts (pins/receptacles). The set of contacts for each group are physically and electrically isolated from the other group by a separator member. This separation provides electrical safety. However, effective electrical separation is not achieved if the connector is not properly seated within the receptacle.

Thus, there is a need to produce a connector which is designed to limit the mating capabilities between the generator and hand piece so that only a hand piece of a preferred type may be properly aligned and mated with the generator so as to ensure optimum performance and results.

SUMMARY OF THE INVENTION

The present invention is directed to a customized connector assembly for providing a secure electrical connection between a surgical hand piece and a power source, e.g., a generator. Preferably, the surgical hand piece comprises an ultrasonic cutting instrument for facilitating the performance of surgical procedures, such as simultaneous soft tissue dissection and cauterization of large and small blood vessels through the use of a precisely controlled ultrasonically vibrating blade or scalpel. The generator is of an ultrasonic type and is designed to produce an electrical signal of a particular voltage, current and frequency. The electrical (generator) signal is applied to a transducer disposed within the hand piece and longitudinally vibration of the elements of the hand piece is effectuated. More specifically, the transducer is connected to the surgical blade by a member so that the surgical blade will therefore be vibrated at ultrasonic frequencies when the generator signal is applied to the transducer. The structure is designed to resonate at the selected frequency, thus amplifying the motion initiated by the transducer.

The connector assembly of the present invention includes a first member which is connected at one end of the cable opposite to the hand piece. The first member comprises a partially hollow member for routing wires of the cable through the first member and into the connector once the connector is sealingly coupled to the first member. The first member has a number of features which permit the user to easily grip the first member. At one end thereof, the first member has a resilient skirt with a cavity formed therein. The cavity is designed to receive a second end of the connector. The resilient skirt is disposed about the connector in a sealing manner so as to shield the electrical wires of the cable.

The first member also includes a resilient arm extending therefrom which connects the first member to an end cap member. The resilient nature of the arm permits the arm to be manipulated and bent to permit the end cap member to be aligned and inserted within a first end of the connector. The end cap member is contoured at one end for the user to grip and at an opposite end, the end cap member has a resilient flange. The resilient flange is sized to be received within a cavity formed at the first end of the connector to ensure that a compressed seal is provided when the end cap member is inserted into the connector. This seal is an optional feature which is attractive because surgical instruments, including the cable and connector assembly of the present invention, are typically subjected to post surgical cleaning processes in which a cleaning solution is used to bath the instruments. This cleaning solution is often corrosive and can damage internal components contained within the connector if continued exposure results. Advantageously, the first member along with the resilient arm and the end cap member are all integrally formed relative to one another and are preferably formed of suitable plastics materials which provide the desired resiliency and strength required for the normal use thereof.

The connector preferably comprises a rigid plastics member which receives electrical cable wires at the first end. The connector has an outer shell and includes an interior wall disposed within the connector. The interior wall extends between the outer shell and is designed to partition the interior of the connector into first and second cavities with the first cavity being at the first end and the second cavity being at the second end. Preferably, the interior wall traverses the outer shell so that it is substantially perpendicular to an inner surface of the outer shell. The interior wall has a plurality of first openings formed therethrough which receive first electrical conductors (first pins) and a plurality of second openings formed therethrough for receiving second electrical conductors (second pins). The precise number and arrangement of the first and second openings will vary depending upon the specific application. The electrical conductors have a length such that a portion of each conductor extends into the first and second cavities.

According to one aspect of the present invention, the connector includes an isolation barrier which is preferably integrally formed with the other portions of the connector. The isolation barrier comprises a member formed on both surfaces of the interior wall so that a first section of the isolation barrier is disposed within the first cavity and extends towards the first end. A second section of the isolation barrier is disposed within the second cavity and extends towards the second end of the connector. Preferably, the isolation barrier is substantially perpendicular to the interior wall. The isolation barrier provides an insulative wall between the first and second electrical circuits housed within the connector. More specifically, the isolation barrier extends between the outer shell of the connector and serves to separate the first conductive pins from the second conductive pins. In the second cavity, the first and second conductive pins are typically electrically connected to other electrical devices, e.g., an EEPROM, and thus the isolation barrier is designed to separate these electrical devices from one another.

In another aspect of the present invention, the connector includes a keying feature formed in the outer surface of the connector. The keying feature comprises an elongated planar indentation formed in the outer surface of the connector. The keying feature orients the connector so it can be electrically plugged into the mating receptacle in only one way. This ensures that the first and second conductive pins are properly mated with matching receptacle electrical ports. This eliminates the risk that the connector will be incorrectly and forcibly mated with the generator resulting in the conductive pins being damaged, i.e. bent. The isolation barrier also provides a unique keying function as the mating receptacle must accommodate the isolation barrier when the connector is plugged therein. In the other words, the mating receptacle must have a slot or the like formed therein to receive the isolation barrier.

In yet another aspect of the present invention, the present connector provides improved separation between the non-isolated set of contacts (pin/receptacles) and the isolated set of contacts (pins/receptacles). In one embodiment this is provided for by reducing the lengths of one set of the electrical pins; namely, the non-isolated pins are preferably recessed deeper in the connector so that the isolated pins mate first with the corresponding isolated receptacles. Due to the electrical configuration of the connector, electrical power is not provided to the hand piece until the non-isolated pins mate with corresponding non-isolated receptacles. This requires the connector to be further disposed within the receptacle and thus ensures that a proper electrical connection is made therebetween.

The connector of the present invention permits easy and convenient mating between the preferred surgical cutting instrument and the accompanying preferred generator which was designed to be used with such preferred surgical cutting instrument. This ensures that the generator will be used with the hand piece which was designed to mate with it and thus a preferred mating arrangement results.

BRIEF DESCRIPTION OF THE DRAWINGS

The foregoing and other features of the present invention will be more readily apparent from the following detailed description and drawings of an illustrative embodiment of the invention in which.

DESCRIPTION OF ILLUSTRATIVE
EXEMPLARY EMBODIMENTS

Figure 1:
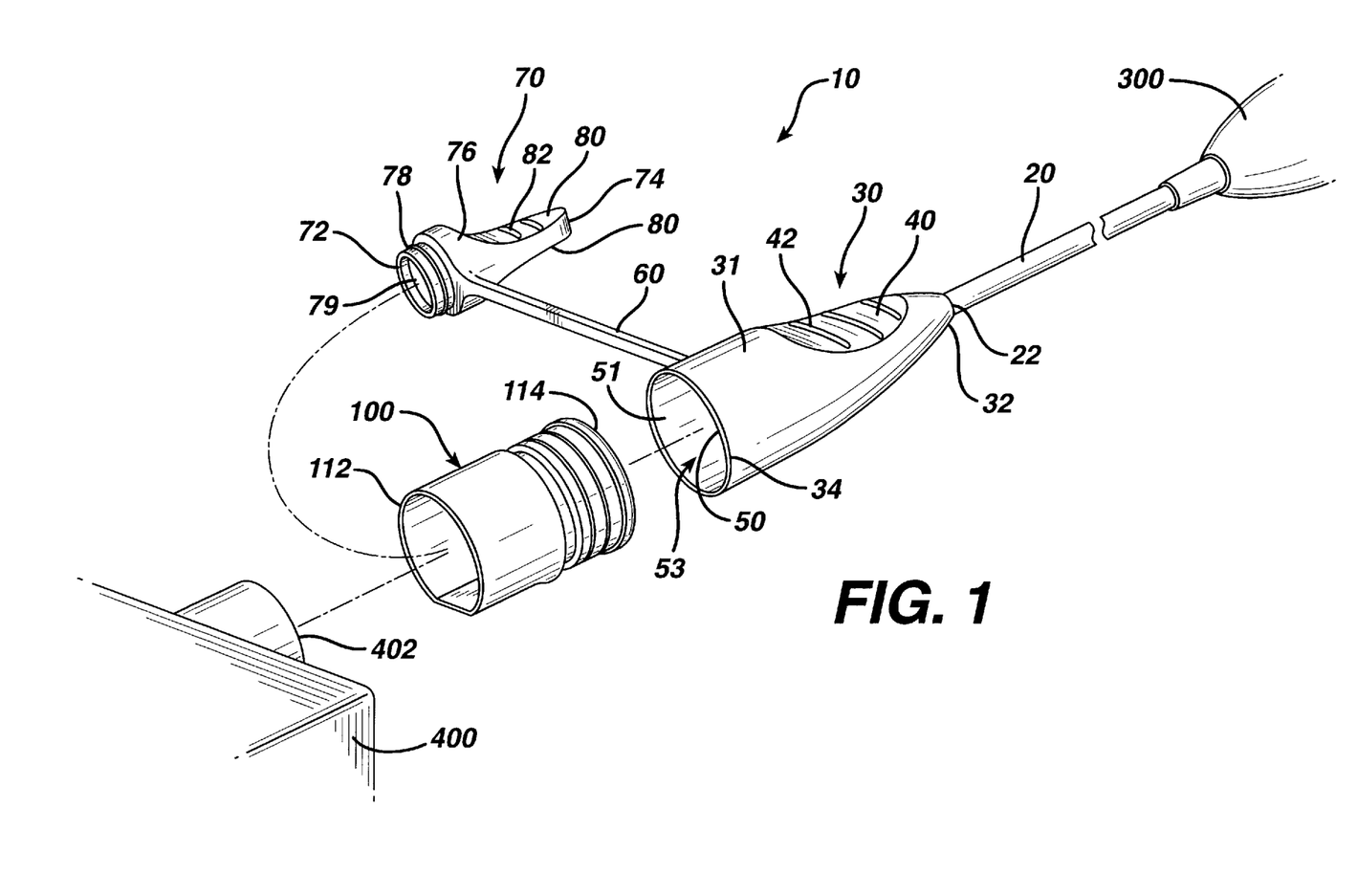
FIG. 1 is an exploded perspective view of a connector assembly according to one exemplary embodiment of the present invention.

Referring first to FIG. 1 in which an exemplary connector assembly according to the present invention is illustrated and generally indicated at 10. The assembly 10 includes a cable 20 which connects at one end to a surgical instrument 300 (partially shown) and connects at another end 22 to a first member, generally indicated at 30.

In turn, member 30 is assembled with a connector 100. The assembly 10, which comprises the member 30 and the connector 100, can be plugged into a plug 402 of a generator 400, preferably an ultrasonic generator. A first end 32 of the first member 30 receives the end 22 of the cable 20 and typically houses other electrical components (not shown) for providing an electrical connection between the cable 20 and a connector 100 according to the present invention. The first member 30 is at least partially hollow so as to permit the cable 20 to pass at least partially therethrough and to permit other electrical components to be disposed within the first member 30. An outer surface 31 of the first member 30 is preferably formed to include depressed gripping sections 40 which are preferably spaced about 180° apart from one another (only one being shown in FIG. 1). The depressed gripping sections 40 preferably each include a number of raised ribs 42 which provide a frictional gripping surface.

The depressed gripping sections 40 are designed as user gripping indents such that the user will typically have a thumb in contact with one of the depressed gripping sections 40 and one or more fingers in contact with the other of the depressed gripping section 40. For example, the user may place several fingers on one section 40 opposite the thumb section 40 and an index finger may be aligned with the axis of the member 30. The size, e.g., lengths, of the depressed gripping sections 40 may be different with respect to one another. For example, one of the depressed gripping sections 40 will preferably have a greater length than the other of the depressed gripping sections 40. In the contemplated use of the system 10, the user will place the index finger in the depressed gripping section 40 having the greater length since the longer length permits the index finger to be positioned along a substantial length of the first member 30. The index finger provides more of a backbone type support and the thumb engages the shorter gripping section 40 during such gripping action. The depressed gripping sections 40 thus permit the user to grippingly engage the first member 30 and permit the user to easily manipulate the first member 30 and the cable 20 attached thereto.

The illustrated first member 30 has a generally tapered design which tapers inwardly toward the first end 32 where the first end 22 of the cable 20 is received. In general, the first member 30 has an annular shape with the exception being that the depressed gripping sections 40 are concave in nature. The first member 30 preferably has a resilient skirt 50 formed at a second end 34 opposite the first end 32. The resilient skirt 50 is designed to sealingly mate with the connector 100 as will be described in greater detail hereinafter. At the resilient skirt 50, the first member 30 preferably has a greater interior volume so that the resilient skirt 50 may receive a portion of end 114 of the connector 100 such that the resilient skirt 50 is disposed thereabout. In other words, a cavity 53 is formed and is defined by the resilient skirt 50, which comprises a thin sheath of material for placement about the end 114 of the connector 100. One will appreciate that the resilient skirt 50 preferably includes one or more retaining features (not shown) such as annular ribs formed on an inner surface 51 of the resilient skirt 50. These further retaining features mate with complementary retaining features 122 formed on the outer surface of the connector 100 (FIG. 2) and are designed to provide an improved seal between the first member 30 and the connector 100.

The first member 30 further includes a resilient arm 60 which extends away from the outer surface 31 of the first member 30 and, for improved structural support, is preferably located between the depressed gripping sections 40 and the formation of the cavity 53 of the resilient skirt 50. The resilient arm 60 serves to connect the first member 30 to an end cap member 70 which is designed to mate with end 112 of the connector 100 opposite the end 114 which is coupled to the resilient skirt 50 (as indicated in FIG. 1 by the broken lines). The end cap member 70 has a first end 72 and an opposing second end 74 with the resilient arm 60 being connected to the end cap member 70 proximate the first end 72. The end cap member 70 includes a body section 76 having a flange 78 at the first end 72. The body section 76 is contoured to be gripped by the user and thus includes opposing depressed gripping sections 80 which are preferably 180° apart from one another. Gripping sections 80 are similar to gripping sections 40; however, the gripping sections 80 extend completely to the second end 74. The gripping sections 80 also preferably have an identical shape relative to each other and further include a number of raised ribs 82 to aid the user in gripping the end cap member 70. Once again, the gripping sections 80 are contoured for receiving the thumb and index finger (or other finger(s)) of the user.

The end cap member 70 is preferably solid yet resilient with the exception that the flange 78 comprises an annular flange extending from the solid section of the end cap member 70. The flange 78 is resilient in nature and has an opening at one end so that a cavity 79 is formed within the flange 78. The flange 78 preferably has an outer diameter which is slightly less than an inner diameter of the end 112 of the connector 100 so that the flange 78 is received within the connector 100 when end cap member 70 engages the connector 100, as will be described in greater detail hereinafter. The end cap member 70 is also known as a soak cap and provides protection for the electrical components contained within the connector 100 during a post surgical cleaning process by sealingly mating with the connector 100. The end cap member 70 is therefore formed of a material that when installed into a cavity formed in the connector creates a compressed seal that provides protection to the electrical components disposed within the cavity. A conventional soak cap is usually separate from the connector and tends to be cumbersome and difficult. The present invention overcomes these deficiencies by making the soak cap (end cap member 70) an integral, attached part of the connector assembly instead of being a separate component. It will be appreciated that the end cap member 70 does comprise an optional feature according to the present invention.

The first member 30 along with the resilient arm 60 and the end cap member 70 are preferably formed of a plastics material, e.g., thermoplastic. More specifically, the plastics material used to form these members preferably comprises a resilient rubber-like material and in one exemplary embodiment, the members are formed by a suitable injection molding process using a liquid injection mold material. The resilient nature of the first member 30 ensures that the first member 30 can be used to sealingly mate with the connector 100. The arm 60 needs to be of a resilient nature so that the arm 60 may be easily bent and manipulated so as to align and introduce the end cap member 70 into one end 112 of the connector 100. In addition, the skirt 50 should be of a resilient nature so that the skirt 50 may be fitted around the other end 114 of the connector 100 so as to produce a seal between the skirt 50 and the connector 100. In yet another aspect of the present invention, the end cap member 70 is preferably formed of the same material as is used to form the first member 30.

Referring now to FIGS. 2–5 in which the exemplary hand piece connector 100 is illustrated. The connector 100 is formed of an outer shell 110 having a first end 112 and an opposing second end 114. Both the first and second ends 112, 114, respectively, are at least partially open and permit access to an interior 116 of the connector 100. The outer shell 110 has an inner surface 118 and an outer surface 120. In the illustrated embodiment, the outer shell 110 has a generally annular shape and thus the interior 116 generally comprises an annular chamber. The outer shell 110 may generally be thought to include three sections, namely a first section 130, a second section 140, and a third section 150 with the second section 140 being disposed between the first and third sections 130, 150, respectively. The second section 140 is an intermediate section of the connector 100, the first section 130 includes the first end 112, and the third section 150 includes the second end 114.

As will be described in greater detail hereinafter, the diameter of the connector 100 is greatest at the second section 140 and is smallest at the third section 150. The third section 150 has a number of locking features for permitting the second end 114 of the connector 100 to be sealingly mated with the first member 30. In particular, the outer surface 120 has formed thereon a plurality of ribs 122 defined by a plurality of channels 124 formed between the plurality of ribs 122. In other words, the plurality of channels 124 are in the form of notches which define the plurality of ribs 122. Because of the annular shape of the outer shell 110, the plurality of channels 124 and the plurality of ribs 122 are also annular in shape. The plurality of ribs 122 and the plurality of channels 124 provide engaging surfaces which may mate with complementary surfaces and members so as to produce a secure fit between the third section 150 and the first member 30. More specifically, the ribs (not shown) formed on the inner surface 51 of the resilient skirt 50 engage the plurality of channels 124 to locate and retain the resilient skirt 50 relative to the connector 100. The resilient skirt 50 thus preferably seats against upper surfaces of the plurality of ribs 122 in a sealing manner when the resilient skirt 50 is disposed about the connector 100.

A first shoulder 152 is formed adjacent to an innermost rib 122 of the third section 150 opposite the second end 114. The first shoulder 152 includes a shoulder channel 154 formed therein. Once again, because of the annular shape of the outer shell 110, the first shoulder 152 and the shoulder channel 154 (FIG. 4) are also annular in shape. The first shoulder 152 preferably acts as a stop surface for locating the connector 100 relative to the resilient skirt 50 which is secured at the second end 114 and the shoulder channel 154 may provide an engagement channel for retaining the connector 100 and the first member 30. The inner diameter of the third section 150 is preferably uniform with the exception that the inner surface 118 of the connector 100 is slightly recessed at the second end 114 causing the inner diameter to be greater in this recessed section. A second shoulder 156 is formed proximate to the second end 114 and defines a lip 158. The lip 158 has a beveled edge 160 which comprises a portion of the second end 114. The lip 158 is likewise annular in shape and preferably has an outer diameter greater than an outer diameter of any one of the plurality of ribs 122. The lip 158 thus may serve as a retaining lip for securing the connector 100 in place.

The second section 140 of the connector 100 includes an interior wall 142 which extends across the outer shell 110. The interior wall 142 has a plurality of first openings 144 and a plurality of second openings 146 formed therein (see FIG. 3). In the illustrated embodiment, both the first and second openings 144, 146, respectively, have a circular cross-section. The first and second openings 144, 146 provide communication between the first section 130 and the third section 150 of the connector 100 (FIG. 4). In other words, the interior 116 of the connector 100 is partitioned by the interior wall 142 and the interior 116 is generally divided into a first interior cavity 117 extending from the interior wall 142 to the first end 112 and a second interior cavity 119 extending from the interior wall 142 to the second end 114. The interior wall 142 has a first surface 143 which faces the first end 112 and a second surface 145 which faces the second end 114 with the first and second openings 144, 146 extending entirely through the interior wall 142 from the first surface 143 to the second surface 145.

Figure 3:
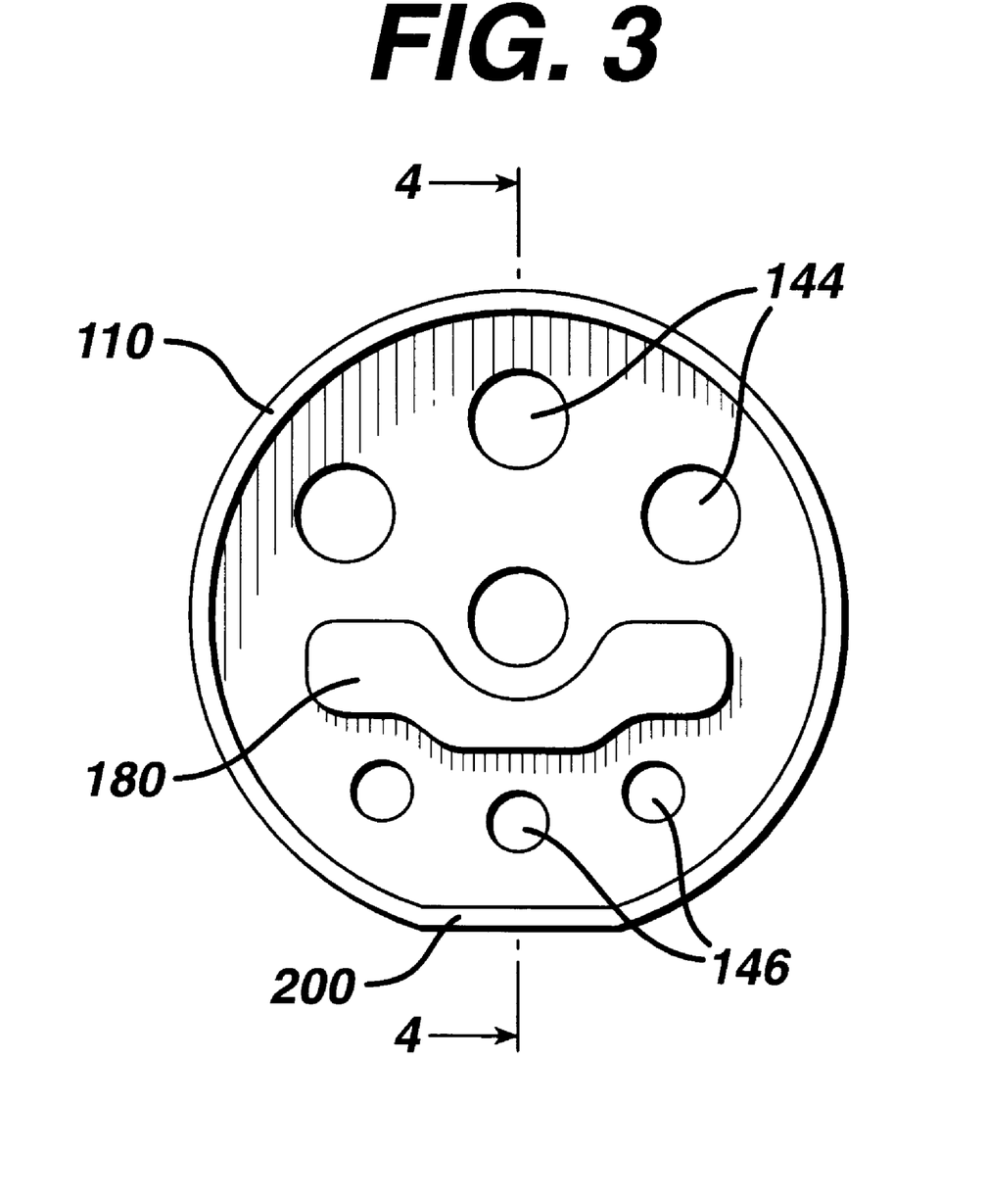
FIG. 3 is a front view of the connector of FIG. 2 shown in the direction of arrow 3—3 of FIG. 2.
Figure 4:
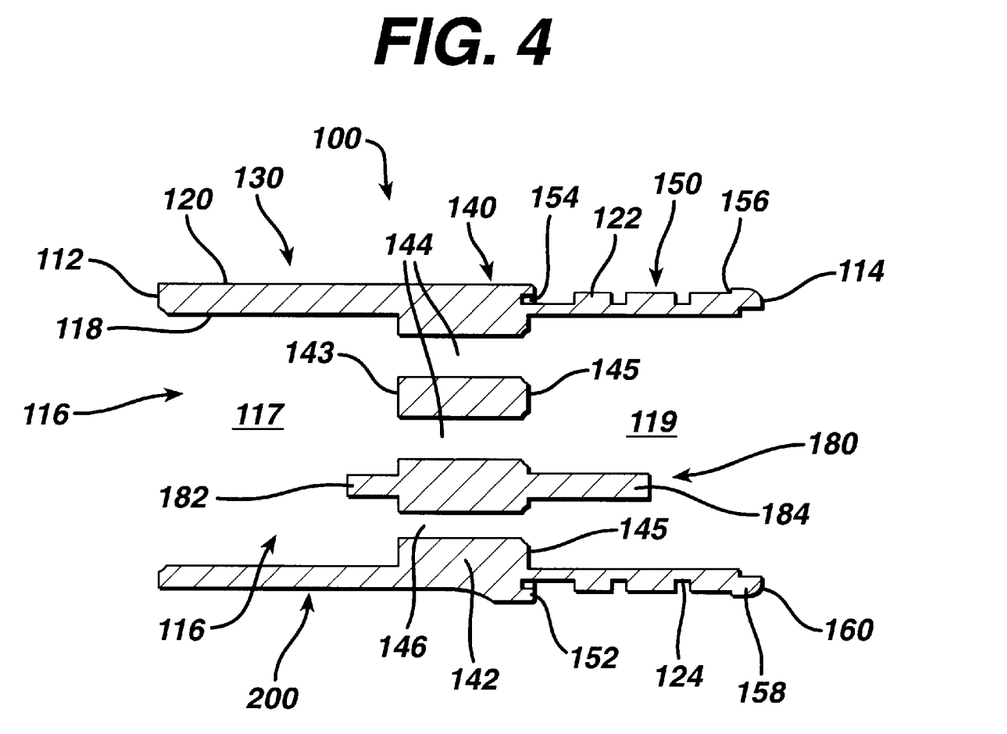
FIG. 4 is a cross-sectional view taken along the line 4—4 of FIG. 3.

As shown in FIG. 3, the particular arrangement of the first and second openings 144, 146 will depend upon the desired application of the connector 100. For purposes of illustration only, the exemplary connector 100 includes four first openings 144 arranged in a generally diamond shaped pattern and three second openings 146 arranged so that a middle second opening 146 is slightly offset from an axis extending through the two other second openings 146. One of skill in the art will appreciate that the number of first and second openings 144, 146 and the arrangement thereof are not critical to the practice of the present invention and will depend greatly upon the precise design of the hand piece and the complementary generator 400.

According to one aspect of the present invention, the interior wall 142 includes an isolation barrier, generally indicated at 180 (FIG. 4). In the illustrated embodiment, the isolation barrier 180 actually comprises a portion of the interior wall 142 and is substantially perpendicular to the first and second surfaces 143, 145, respectively, of the interior wall 142. The isolation barrier 180 is has a first section 182 which extends outwardly from the first surface 143 of the body portion 142 and a second section 184 which extends outwardly from the second surface 145 of the body portion 142. As best illustrated in FIGS. 3 and 4, the isolation barrier 180 provides a structural barrier between the plurality of first openings 144 and the plurality of second openings 146 so as to electrically isolate first electrical components (not shown) disposed through the first openings 144 from second electrical components (not shown) disposed through the second openings 146. The isolation barrier 180 thus has a predetermined size extending between the outer shell 110 to ensure that any one of the first openings 144 is separated from any one of the second openings 146. While FIG. 3 illustrates the isolation barrier 180 as partially extending between the outer shell 110, it will be appreciated that in another embodiment, the isolation barrier 180 extends completely between the outer shell 110.

As will be described in greater detail hereinafter, the isolation barrier 180 is designed to separate electrical components (not shown) which are disposed within the second cavity 119 at the second end 114 of the connector 100. In the illustrated embodiment, the length of each of the first and second sections 182, 184 of the isolation barrier 180 are such that the first section 182 extends only partly towards the first end 112 and the second section 184 extends only partly towards the second end 114. In the illustrated embodiment, the first section 182 has a length less than the length of the second section 184. Because the first and second openings 144, 146 extend completely through the body portion 142, the shapes of the first section 182 and the second section 184 are likely to be identical since each section is configured between the first openings 144 and the second openings 146. However, it is within the scope of the present invention that the first section 182 may have a different shape than the second section 184. The isolation barrier 180 is preferably formed of an insulative material so as to provide a conductive barrier within the interior 116 of the connector 100. Preferably, the isolation barrier 180 is integrally formed with the interior wall 142.

FIG. 3 is a front view showing the first end 112 of the connector 100. This figure best illustrates the arrangement of the plurality of first openings 144, the plurality of second openings 146, and the isolation barrier 180. As shown, the isolation barrier 180 is within the outer shell 110 and ensures that each of the first openings 144 is separated from all of the second openings 146.

Figure 2:
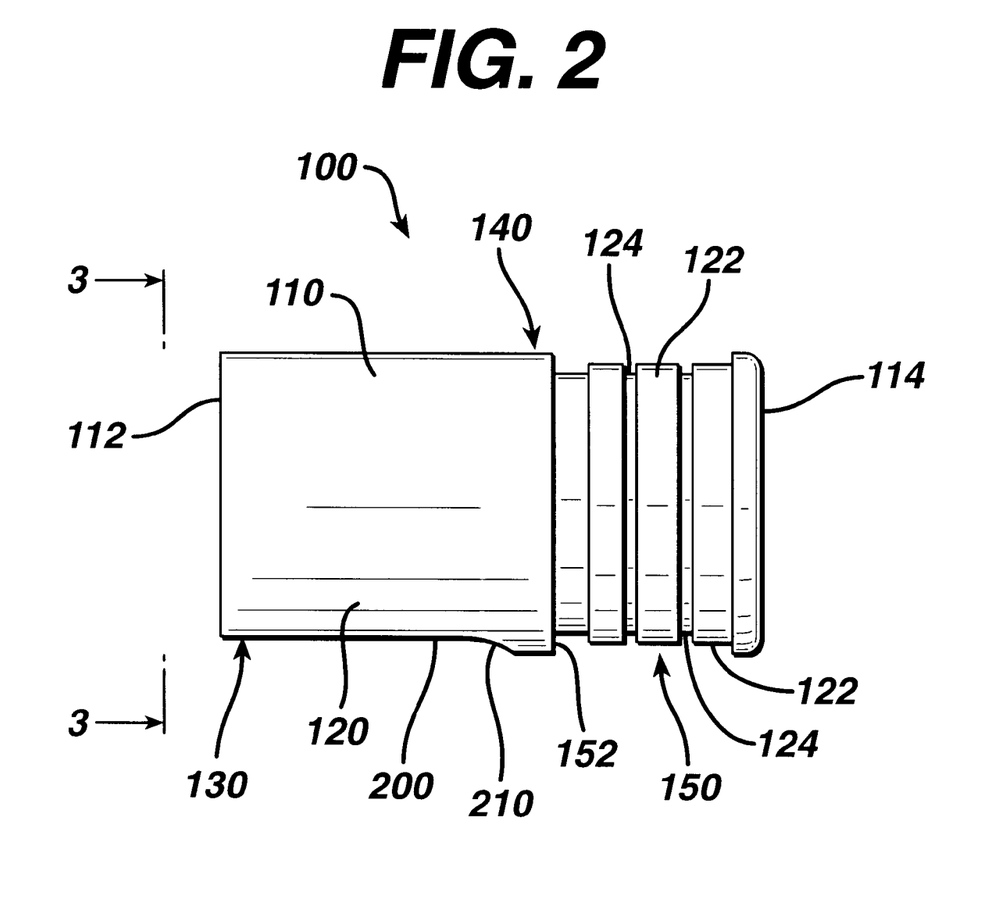
FIG. 2 is a side elevational view of an exemplary connector in accordance with the present invention.
Figure 5:
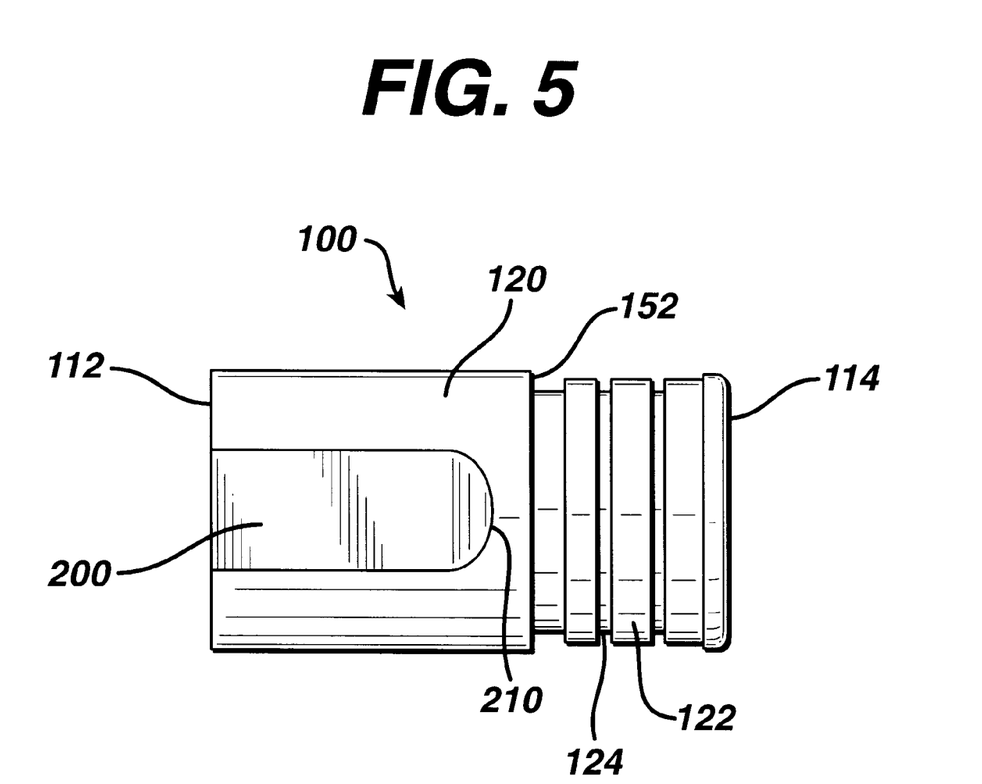
FIG. 5 is another side elevational view of the connector of FIG. 2 showing one feature of the present invention.

As best shown in FIGS. 2 and 5, in another aspect of the present invention, the connector 100 has a keying feature, generally indicated at 200. The keying feature 200 is formed in the outer surface 120 of the connector 100. Generally, the keying feature 200 comprises an indented planar surface formed in the outer surface 120 extending from the first end 112 to a location 210. More specifically, the keying feature 200 extends from the first end 112 and terminates prior to the first shoulder 152 and the plurality of ribs 122. The illustrated keying feature 200 terminates in a beveled edge 210. The keying feature 200 provides a manner of visually and physically orientating the connector 100 for proper insertion into a power source 400, e.g., a generator or the like. For example, the keying feature 200 is formed in the outer surface 120 proximate to the plurality of second openings 146 so that a plane containing the keying feature 200 is generally parallel to a plane extending centrally through the ends of the isolation barrier 180. In this position, the plurality of second openings 146 are disposed between the isolation barrier 180 and the keying feature 200. The keying feature 200 will most likely mate with a tab or ridge (not shown) formed as part of the plug 402 of the generator 400 which provides the electrical connection between the generator 400 and the connector assembly 10. During operation, the connector 100 is plugged into the plug 402 of the generator 400 with the keying feature 200 slidingly receiving the tab or ridge of the generator plug 402.

With reference to FIGS. 1 through 6, during operation, a number of electrical conductors are disposed within the connector 100 so that an electrical connection is made between the generator 400 and the hand piece 300 via cable 20. In the illustrated embodiment, a plurality of first electrical conductors 220 extend through the plurality of first openings 144 with the first electrical conductors 220 being associated with a first circuit. Therefore, in the exemplary embodiment, there are four first electrical conductors 220 which extend through the four first openings 144. The diameter of the first electrical conductors 220 is slightly less than the diameter of the first openings 144 so that the movement of the first electrical conductors 220 is constrained by the interior wall 142 in which the first openings 144 are formed. The first electrical conductors 220 may comprise any number of suitable electrical conductors and in a preferred embodiment, the first electrical conductors 220 comprise conductive pins.

Figure 6:
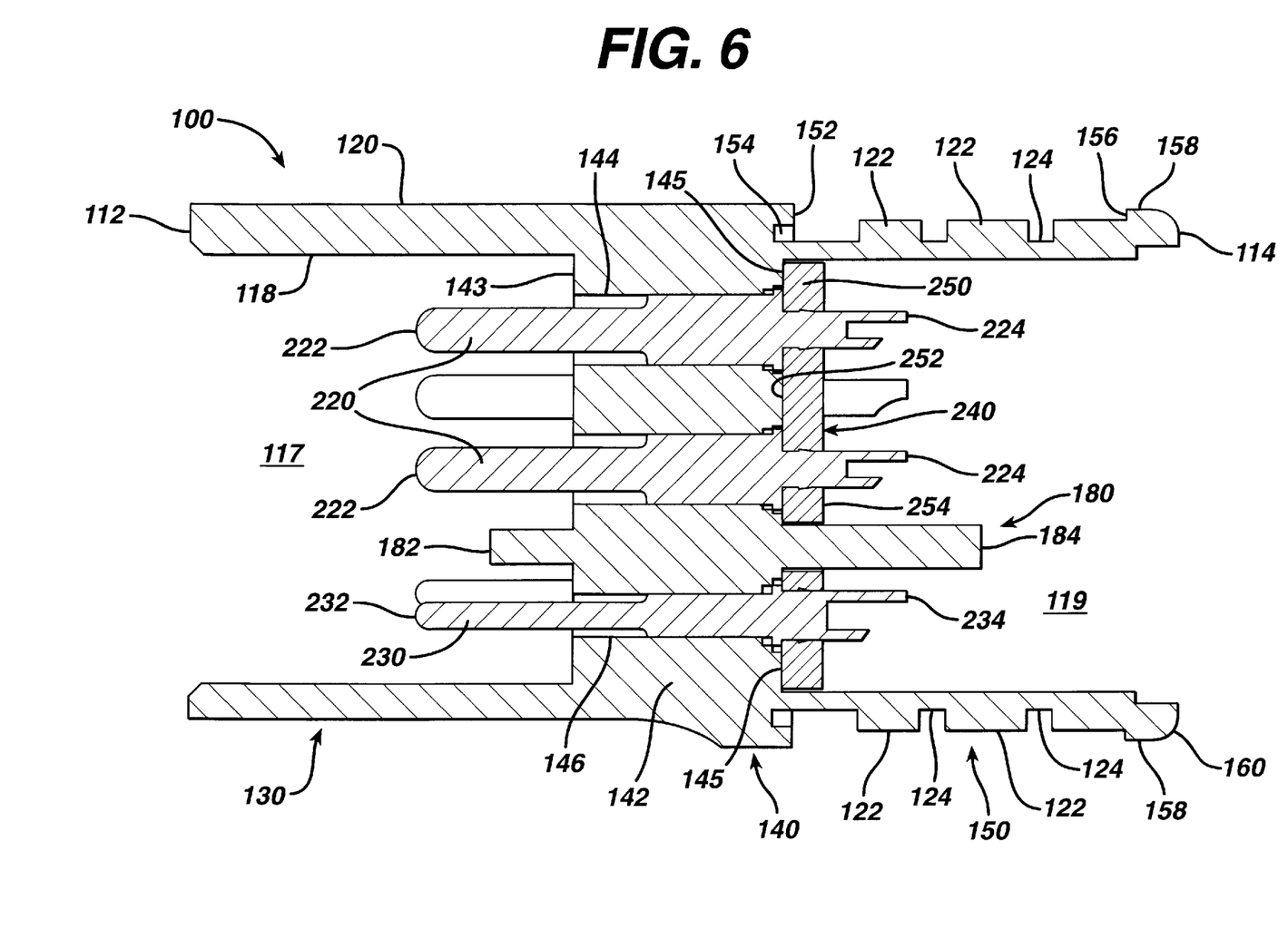
FIG. 6 is a cross-sectional view showing the connector of FIG. 2 with a number of electrical conductors disposed therein.

A plurality of second electrical conductors 230 extend through the plurality of second openings 146 and the second electrical conductors 230 are associated with a second circuit. In the illustrated embodiment, there are three second electrical conductors 230 in the form of electrical pins. Typically, the first and second electrical conductors 220, 230 will vary in terms of sizes; however, the general shape (in this case pin shape) will usually be the same. It will be appreciated that the number and shapes of the first and second electrical conductors 220, 230 may be varied depending upon the precise application. For example, the first conductors 220 may have a first cross-sectional shape and the second conductors 230 may have a different second cross-sectional shape.

Often the first and second electrical conductors 220, 230 form a part of a conductor header assembly, generally indicated at 240. The conductor header assembly 240 has a non-conductive base portion 250 to which the first and second electrical conductors 220, 230 are connected and extend outwardly therefrom. The base portion 250 preferably has a cross-sectional shape which is complementary to the cross-sectional shape of the connector 100. In this case, the base portion 250 is generally an annular member which is disposed within the connector 100 and more specifically a first surface 252 seats against the second surface 145 of the interior wall 142. The first and second electrical conductors 220, 230 extend away from the first surface 252 with first ends 222, 232, respectively, being for reception in a complementary member, such as an outlet (not shown) of the generator 400, so as to provide an electrical connection therebetween. Second ends 224, 234 of the first and second electrical conductors 220, 230, respectively, extend away from a second surface 254 of the base portion 250. The second ends 224, 234 comprise terminal portions which are typically connected to electrical wires (not shown) which form a part of the cable 20. It will be appreciated that the second ends 224 are connected to electrical wires associated with the first electrical component (first circuit) and the second ends 234 are connected to electrical wires associated with the second electrical component (second circuit). The attachment between the second ends 224, 234 and the electrical wires may be accomplished by any number of suitable techniques including soldering the electrical wires to the second ends 224, 234.

In addition, the connector 100 and more specifically, the second cavity 119 thereof provides an area for additional electrical components to be mounted within the connector 100. One type of electrical component that is contemplated for use in the connector 100 is an electrically erasable programmable read-only memory (EEPROM) (not shown). As is known, an EEPROM is generally an integrated-circuit memory chip that has an internal switch to permit a user to erase the contents of the chip and write new contents into it by means of electrical signals. It will be appreciated that an EEPROM is merely one exemplary type of electrical component that may be used. The present invention is thus not limited to only this type of application. When an EEPROM is used, the EEPROM is electrically connected to the second ends 224 or 234 of the respective electrical conductors 220 or 230 to which the EEPROM is related. It will be understood that the EEPROM is preferably connected prior to the conductor header assembly 240 being disposed within the connector 100 against the interior wall 142. This second cavity 119 thus provides a proprietary interface storage of hand piece data and enables/disables generator functions.

In addition, one will appreciate that the isolation barrier 180 provides a unique keying functioning in and of itself because the mating receptacle of the generator 400 must accommodate the isolation barrier 180 when the connector 100 is plugged therein. In other words, the mating receptacle must have a slot or the like (not shown) formed therein to receive the isolation barrier 180. The shape of the isolation barrier 180 thus provides a unique key which fits only into a generator receptacle having a complementary design.

According to the present invention, the connector 100 is preferably machined or molded from a high temperature engineered plastic and preferably is rigid in design. For example, the connector 100 may be formed of a suitable thermoplastic material and in one embodiment, the connector 100 and the features thereof are formed using a suitable molding process in which the thermoplastic material is passed through a die assembly (not shown). Accordingly, all of the illustrated features of the connector 100 are preferably integral with one another so that the connector 100 comprises a single member.

The connector assembly 10 of the present invention provides a unique interface to a selected, preferred generator as well as other benefits to the user. For example, the incorporation of the soak cap 70 as part of the member which receives and mates with one end of the connector 100 provides several advantages to the user and the isolation barrier partitions the connector 100 so that the different electrical components are separated from one another to avoid any cross electrical connections (which would likely cause a short). In general, the connector assembly 10 offers an attractive, intuitive, user friendly, and robust design.

Figure 7:
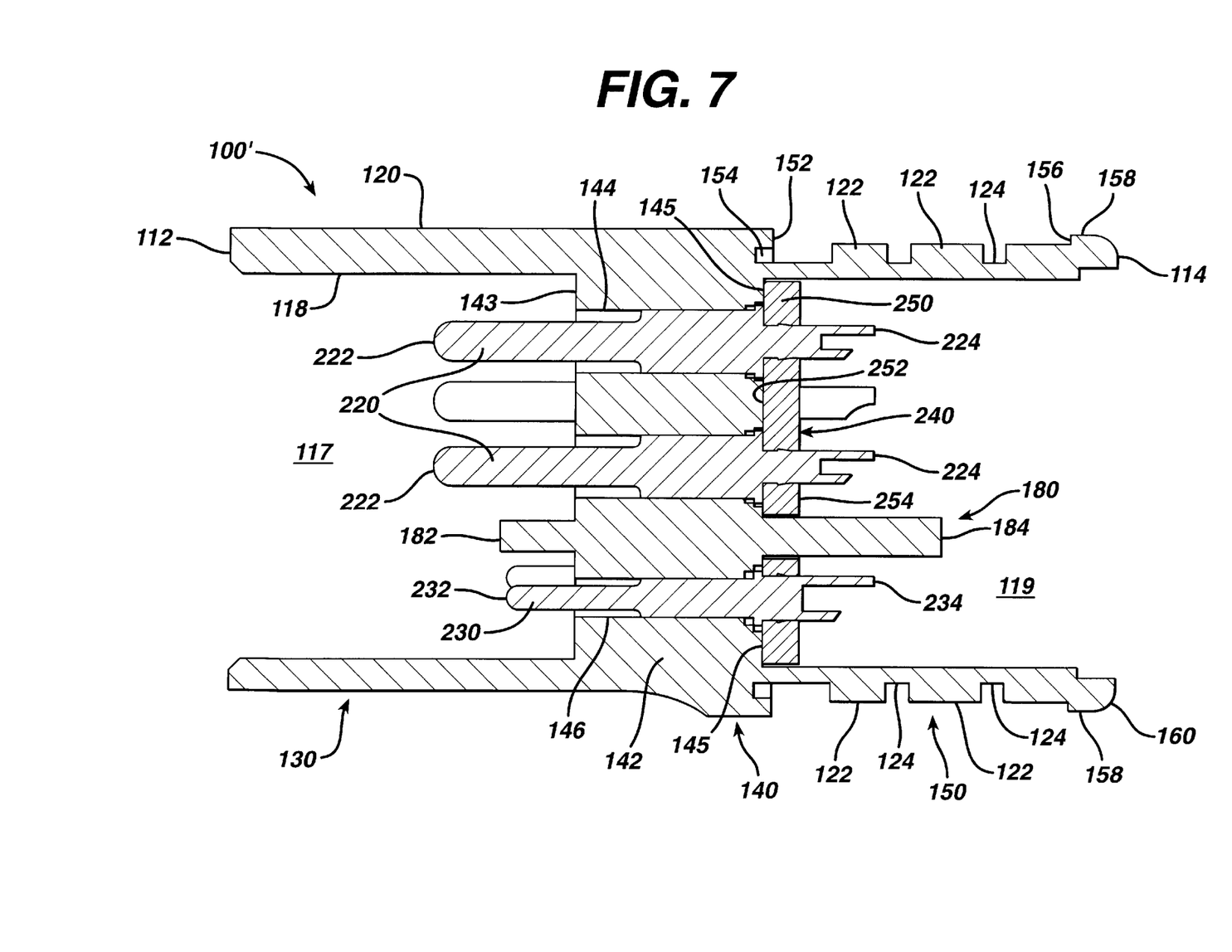
FIG. 7 is a cross-sectional view showing a connector according to another embodiment of the present invention.

Now referring to FIG. 7 in which a connector according to another embodiment is illustrated and generally indicated at 100'. Connector 100' is similar to the connector 100 with the exception that one of the sets of electrical pins 220, 230 has a length less than the length of the other set of electrical pins 220, 230. As previously-mentioned, separation between the electrical pins 220, 230 is necessary for providing electrical safety. One of the sets of electrical pins 220, 230 comprises non-isolated electrical pins which are referenced to ground and the other set of electrical pins 220, 230 comprises a patient isolated set of electrical pins. The desired separation between the electrical pins 220, 230 is accomplished by means of an elongated path profile of the mating connector and receptacle. The isolation barrier 180 is dependent upon on a fully seated connector into the receptacle to assure an adequately long path length along surfaces to meet applicable isolation requirements. For example, this separation assures that "patient isolation requirements", which are set forth under governing medical electrical safety standard, are met. Such safety separation is also required in other electrical safety standards for non-medical devices also. If the connector 100 is not fully inserted into the receptacle 402 (FIG. 1), then it is possible to operate the surgical instrument 300 without the benefit of a fully seated isolation barrier 180. Thus, the isolation barrier 180 is not adequately long and the isolation requirements are not met. This could be the case if the user is not following instructions correctly when plugging in the connector 100. In such a scenario, the user would be able to activate the surgical instrument 300 and apply power to the surgical instrument 300 without the intended isolation barrier 180 adequately in place.

The present invention provides a solution which is designed to promote proper insertion of the connector 100 into the receptacle 302. In one exemplary embodiment shown in FIG. 7, one of the set of electrical conductors 220, 230 are recessed deeper within the first interior cavity 117 than the other set of electrical conductors 220, 230. Preferably, the non-isolated electrical conductors (pins) which act as control pins are recessed deeper than the patient isolated electrical conductors (pins) which drive the hand piece transducer (not shown). For purpose of illustration only, the first electrical conductors 220 comprise the patient isolated electrical conductors and the second electrical conductors 230 comprise the non-isolated electrical conductors. The non-isolated electrical conductors (the second electrical conductors 230) are used to detect the presence of a hand piece (not shown) plugged in and when detected, enable the user's ability to activate the hand piece. The non-isolated electrical conductors 230 can be connected to an EEPROM in the hand piece or the conductors 230 may be strapped together or a resistor may be placed between the conductors 230. Circuitry inside the generator (not shown) is used to detect the presence of the EEPROM or the strap or the resistor across the non-isolated conductors 230. The sensing of the presence of the connector 100' can be by means of a wire strap across pins in the non-isolated conductor group which is detected by a sensing circuit, such as resistance measurement, connected to the receptacles associated with the mating receptacles. The sensing can also be by means of an EEPROM in the connector 100' that is connected to the conductors 230 in the non-isolated conductor group which is detected by an EEPROM reader connected to the associated mating receptacle.

Accordingly, the length of each of the first electrical conductors 220 is greater than a length of each of the second electrical conductors 230 as shown in FIG. 7. In this embodiment, the first section 182 of the isolation barrier 180 does not extend to the end of the first electrical conductors 220. In other words, a portion of the first electrical conductors 220 extends beyond an end of the first section 182. When mating the connector 100' with the receptacle 402, the first electrical conductors 220 will make contact first and be engaged with the corresponding receptacles of the receptacle 402 because the first electrical conductors 220 have a greater length.

Unlike in conventional designs, when the connector 100' is partially plugged into the receptacle 402, activation of the hand piece is not enabled because the more recessed set of non-isolated second electrical conductors 230 have not yet made contact. This prevents the use of an inadequately plugged-in and inadequately isolated connector 100'. When the connector 100' is adequately engaged into the receptacle 402 to meet isolation requirements, the non-isolated second conductors 230 have engaged the receptacle 402, providing indication that there is adequate physical/electrical separation of the patient isolated contacts (first conductors 220) from the non-isolated contacts (second conductors 230).

In another embodiment, the patient isolated contacts 220 and the non-isolated contacts 230 each have the same length; however, the length of the first section 182 is increased so that the first section 182 extends beyond the ends of each of the contacts 220, 230. This ensures that adequate separation is achieved. This particular embodiment is effective; however, requires larger/longer connectors to implement this method. This may not be ideal in all applications. Another method that aids in ensuring that the connector 100' has been adequately seated into the receptacle is to utilize an audible/tactile indicator that provides feedback to the user that the connector 100' has been adequately pushed in to meet isolation criteria. For example, a latching mechanism or a ball-snap-into-a-seat design may be used so long as it provides the audible and/or tactile feedback to the user.

While the invention has been particularly shown and described with reference to preferred embodiments thereof, it will be understood by those skilled in the art that various changes in form and details may be made therein without departing from the scope of the invention.

What is claimed is:

1. A connector for electrically connecting an instrument to a power supply, the connector comprising:

an outer shell having a first end and an opposing second end;

an interior wall extending across the outer shell intermediate to the first and second ends, the interior wall having a plurality of first and second openings formed therethrough, the interior wall partitioning an interior of the outer shell into a first cavity extending to the first end and a second cavity extending to the second end;

a plurality of first electrical conductors extending through the plurality of first openings such that free tips ends thereof are located in the first cavity, the first electrical conductors being electrically connected to the instrument;

a plurality of second electrical conductors extending through the plurality of second openings such that free tips ends thereof are located in the first cavity, the second electrical conductors being electrically connected to the instrument; and an isolation barrier disposed within the outer shell and extending from a first surface of the interior wall into the first cavity so as to separate each of the first electrical conductors from each of the second electrical conductors.

2. The connector as in claim 1, wherein the isolation barrier has a length less than a diameter of the outer shell, the isolation barrier having first and second ends spaced a distance from the outer shell.

3. The connector as in claim 1, wherein the isolation barrier has a first section extending from the first surface into the first cavity and a second section extending from a second surface of the interior wall into the second cavity.

4. The connector as in claim 1, wherein the isolation barrier is integrally formed with the interior wall.

5. The connector as in claim 1, wherein the connector is formed of a thermoplastic material and comprises a unitary molded member.

6. The connector as in claim 1, wherein the first and second electrical conductors comprise electrical pins.

7. The connector as in claim 1, wherein the connector further includes:
a non-conductive base in which the plurality of first and second electrical conductors are connected thereto and extend away from first and second surfaces thereof, non-conductive base being seated against the first surface of the interior wall when the connector is assembled, the non-conductive base having an opening for accommodating the isolation barrier.

8. The connector as in claim 1, wherein the instrument comprises an ultrasonic surgical instrument.

9. The connector as in claim 1, wherein the connector further includes:
a keying feature formed on an outer surface of the outer shell.

10. The connector as in claim 9, wherein the keying feature comprises an elongated planar indented surface.

11. The connector as in claim 9, wherein the keying feature extends from the first end to a location prior to the second end.

12. The connector as in claim 9, wherein the keying feature has a beveled inner edge which serves as a stop.

13. The connector as in claim 1, wherein each of the first electrical conductors has a first length and each of the second electrical conductors has a second length, the first length being greater than the second length.

14. The connector as in claim 13, wherein the connector is adapted to be inserted into a complementary receptacle, the first electrical conductors comprising isolated contacts which serve to drive the instrument and the second electrical conductors comprise non-isolated contacts which are referenced to ground and detect presence of the instrument being matingly received in the receptacle, whereby the presence of the instrument is not detected until the shorter second electrical conductors are inserted into the receptacle.

15. A connector assembly for electrically connecting an instrument to a power supply, the connector assembly comprising:
a first member having a body for attachment to one end of an electrical cable which connects at an opposite end to the instrument, the first member having a resilient arm integrally formed as part of the body at one end thereof, the resilient arm having an end cap member formed at an outer end thereof;
a removeable connector formed of an outer shell having a first end and an opposing second end, the connector having a plurality of first and second electrical conductors disposed within the outer shell with an isolation barrier extending internally between the outer shell so as to separate each of the first electrical conductors from each of the second electrical conductors; and
wherein the first member has a resilient skirt section defining a cavity which receives the second end of the connector, the resilient skirt section sealingly mating with the second end of the connector, the end cap member being received within the first end of the connector to form a seal therewith for protecting the first and second electrical conductors under select conditions.

16. The connector assembly as in claim 15, wherein the first and second electrical conductors comprise conductive pins.

17. The connector assembly as in claim 15, wherein the outer shell includes a plurality of channels formed on an outer surface thereof for engaging complementary ribs formed on an inner surface of the resilient skirt section so as to locate and seal the resilient skirt about the outer shell.

18. The connector assembly as in claim 15, wherein the end cap member includes a resilient flange at one end which is received within the first end of the connector to form the seal.

19. The connector assembly as in claim 15, wherein the first member including the resilient arm and end cap member form a resilient unitary member.

20. The connector assembly as in claim 15, wherein the connector further comprises:
an interior wall extending between the outer shell intermediate to the first and second ends, the interior wall having a plurality of first and second openings formed therethrough, wherein the plurality of first electrical conductors extend through the plurality of first openings and the plurality of second electrical conductors extend through the plurality of second openings.

21. The connector assembly as in claim 20, wherein the interior wall partitions the connector into a first cavity extending to the first end and a second cavity extending to the second end, the first and second electrical conductors each having a first end extending into the first cavity for reception in an outlet of the power supply and a second end for electrical attachment to the electrical cable.

22. The connector assembly as in claim 15, wherein the connector further includes:
a keying feature formed on an outer surface of the outer shell, the keying surface for orienting the connector relative to the power supply so that the first and second electrical conductors properly mate therewith to provide power to the instrument.

23. The connector assembly as in claim 22, wherein the keying feature comprises an elongated planar indented surface.

* * * * *